United States Patent [19]

Langlais

[11] Patent Number: 4,950,300
[45] Date of Patent: Aug. 21, 1990

[54] HIP PROSTHESIS WITH INTERCHANGEABLE EPIPHYSUS

[75] Inventor: Frantz Langlais, Rennes, France

[73] Assignee: OMCI SA, Quimper, France

[21] Appl. No.: 379,711

[22] Filed: Jul. 13, 1989

Related U.S. Application Data

[63] Continuation of Ser. No. 178,263, Apr. 6, 1988, abandoned.

[30] Foreign Application Priority Data

Aug. 3, 1987 [FR] France ............................. 87 11096

[51] Int. Cl.5 .................................................. A61F 2/36
[52] U.S. Cl. ............................................ 623/23; 623/16
[58] Field of Search ..................... 623/23, 22, 20, 16, 623/18

[56] References Cited

U.S. PATENT DOCUMENTS

| | | | |
|---|---|---|---|
| 3,874,003 | 4/1975 | Moser et al. | 623/23 |
| 3,894,297 | 7/1975 | Mittelmeier et al. | 623/22 |
| 4,404,691 | 9/1983 | Buning et al. | 623/23 X |
| 4,488,319 | 12/1984 | vonRecum | 623/23 |
| 4,608,055 | 8/1986 | Morrey et al. | 623/23 |
| 4,676,797 | 6/1987 | Anapliotis et al. | 623/23 X |
| 4,790,851 | 12/1988 | Suire et al. | 623/16 |

FOREIGN PATENT DOCUMENTS

| | | | |
|---|---|---|---|
| 0011665 | 11/1978 | European Pat. Off. | 623/22 |
| 2580171 | 10/1986 | France | 623/23 |

*Primary Examiner*—Ronald Frinks
*Attorney, Agent, or Firm*—Oblon, Spivak, McClelland, Maier & Neustadt

[57] ABSTRACT

A hip prosthesis with interchangeable epiphysis. The prosthesis is formed from a neck and a head which form a one piece assembly, the neck having a reduced diameter at the level of the head and a greater diameter at its base. The assembly includes a housing for receiving a Morse cone which is integral with the upper pole of the femoral shank. Different sizes of the assembly may be used with different length shanks.

8 Claims, 1 Drawing Sheet

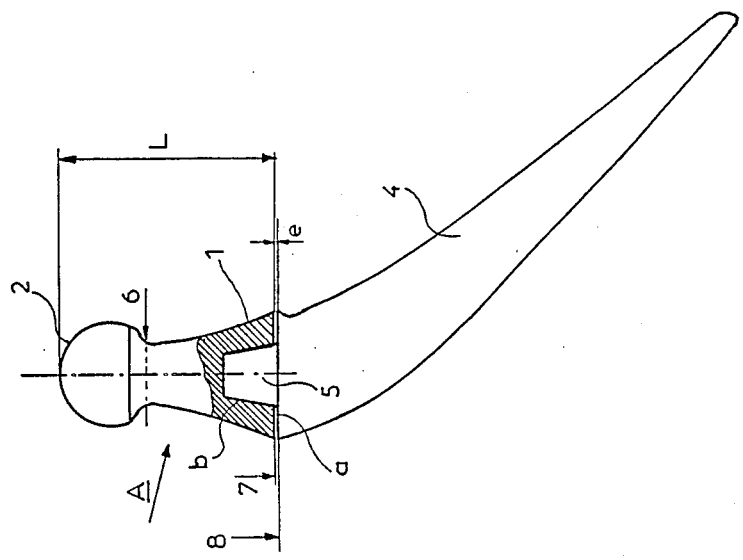

HIP PROSTHESIS WITH INTERCHANGEABLE EPIPHYSUS

This application is a continuation of application Ser. No. 178,263, filed on Apr. 6, 1988, now abandoned.

The invention relates to a hip prosthesis with interchangeable epiphysis.

Femoral prostheses are at present widely used. They are implanted in the upper end of the femur when the femoral head needs to be replaced, in the case more particularly of traumatism or arthritis.

Two types of techniques are used. In one, recourse is had to total hip prosthesis, in which the shank, the neck and the head form a one piece assembly. This technique has numerous drawbacks among which for example the following may be cited:

the impossibility of adjusting the length of the neck after sealing the femoral piece, which requires a considerable stock of test prostheses and final prostheses;

the absence of alternative solution if, during the operation, the head is scored, as if often the case when soft material such as steel is used;

the need to revise the whole femoral shank at the time of renewing the prosthesis for isolated acetabular loosening.

To limit these drawbacks, interchangeable heads have been used fitted to the tapered portion provided therein by means of a Morse cone integral with the shank/neck assembly, which has the further advantage of allowing variable lengths of the neck/head assembly to be obtained through relative penetration of the two parts.

This solution proves relatively satisfactory for heads of large diameter which still make it possible to have necks of sufficient dimensions. On the other hand, it is no longer the case when it is a question of small diameter heads (and so of necks) however, these heads are characterized, at least for the metal/polyethylene pair, by a lifespan considerably longer than that of large diameter heads. It is then advantageous to keep a small diameter head. Unfortunately, in the case of heads 22.2 mm in diameter, more particularly, the solution of the conventional Morse cone can no longer be applied. The taper must in fact be very fine, so as to avoid impingement against the edges of the coloidal cupula, which risks making it abnormally fragile in a zone of maximum stress. In addition, this fineness is incompatible, considering the usual angles of Morse cones, with substantial variations in the lengths of the neck/head assembly.

The purpose of the present invention is to overcome these drawbacks and relates to a new combination of any diameter, for example anatomic size but moreover head of small diameter, to cooperate with a fine prosthetic neck, avoiding impingement with the edges of the acetabular cup, this neck/head assembly mounted on the shank being interchangeable and allowing variations of length.

The invention relates more precisely to a hip prosthesis formed of a femoral shank and an interchangeable epiphysis, characterized in that the head (2) forms with the neck (1) a one piece assembly (8) having at its base a housing intended to receive a Morse cone forming an integral part of the upper pole of the femoral shank.

The invention will be better understood from the following explanations and from the accompanying FIGURE which illustrates a hip prosthesis in accordance with the invention.

According to an important characteristic of the invention, contrary to what exists in interchangeable head prostheses of known type in which the neck is originally integral with the shank and carries the Morse cone, the prosthetic neck (1) of the invention is this time originally integral with the head (2) so as to form a one piece neck/head assembly referenced (A) and intended, during positioning of the prosthesis, to be fixed to the shank 4 while maintaining a clearance e between the base 7 of neck 1 and the upper plane 8 of shank 4.

The central medular shank 4 has at its upper pole a morse cone 5 forming an integral part of the shank and intended to penetrate in a housing b formed at the base of the prosthetic neck 1 forming part of the one piece assembly A. The configuration of this neck 1 is such that, in another characteristic of the invention, its diameter decreases from its base 7 as far as the connection zone 6 of neck 1 with head 2 where its diameter is minimum. The assemblies A may be of different lengths L and be associated with shanks 4 also of different dimensions. Because of the dual characteristic, neck/head connection forming one piece, on the one hand, and dimensioning and shape of the neck itself on the other, a certain number of advantages result.

Mechanical strength is in fact insured: the morse cone 5 is in fact transferred to a region where the parts may be overdimensioned so as to avoid breakage by fatigue. A morse cone of 15 mm in diameter may for example be formed penetrating inside a neck of 30 mm in diameter. Moreover, since the materials chosen are not subjected to tribologic requirements, they may be selected as a function of their resistance to fatigue (titanium alloy cone for example).

The housing (b), being cervical, does not penetrate to the head.

Finally, the binomials may be varied, neck/head (assembly A) on the one hand and shank on the other, as shown in the few examples below:

steel shank, steel neck/head
titanium shank, steel neck/head
titanium shank, nitrided titanium neck/head
titanium shank, titanium neck, ceramic head.

Fixing the ceramic to the neck may be adjusted optimally since it is not at this level that possible extension of the neck will take place and since the contact between these two parts will therefore always take place under optimum conditions.

A not inconsiderable economic advantage is provided by the combination of the invention, since the surgeon will only need to have a set of femoral shanks on the one hand and a set of neck/head assemblies A on the other.

The invention applies to surgical techniques for implanting hip prostheses.

I claim:

1. A hip prosthesis comprising a femoral shank, a neck and a head, characterized in that head (2) forms with the neck (1) a one-piece assembly (A) having at its base a housing (b) that extends in the same direction as the longitudinal axis of the neck and is directed according to the length of the neck, and limited to said neck so that the strength of said head is not effected by the presence of said housing, said housing being provided for receiving a Morse cone (5) forming an integral part of the upper pole (a) of the femoral shank (4) in such a way that continuous circumferential clearance (e) is present between the base (7) of the neck (1) and the upper plane (8) of the shank (4).

2. A hip prosthesis according to claim 1, characterized in that said assembly (A) is selected from a set of assemblies (A) having different lengths (L), and the shank (4) is selected from a set of shanks of different sizes, related to a function of morphological criteria.

3. Prosthesis according to one of claims 1 or 2, characterized in that the dimensioning of the neck (1) is such that its diameter is maximum at its base (7) and minimum at the level of its connection zone (6) with the head (2).

4. Prosthesis according to claim 3, characterized in that the rod (4) and the assembly (A) are made from steel.

5. Prosthesis according to claim 3, characterized in that the shank (4) is made from titanium and the assembly (A) from steel.

6. Prosthesis according to claim 3, characterized in that the shank (4) is made from titanium and the assembly (A) from nitrided titanium.

7. Prosthesis according to claim 3, characterized in that the shank is made from titanium and that in the assembly (A), the neck is made from titanium and the head is made from ceramics.

8. Prosthesis according to claim 1, wherein said assembly is selected from a plurality of different size assemblies.

* * * * *